(12) United States Patent
Teraoka (10) Patent No.: US 6,375,640 B1
(45) Date of Patent: Apr. 23, 2002

(54) WINGED INJECTION NEEDLE DEVICE

(75) Inventor: Yosisuke Teraoka, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

(21) Appl. No.: 09/553,266

(22) Filed: Apr. 20, 2000

(30) Foreign Application Priority Data

Apr. 26, 1999 (JP) .......................................... 11-118683
Sep. 9, 1999 (JP) .......................................... 11-255755

(51) Int. Cl.[7] .............................................. A61M 5/00
(52) U.S. Cl. ...................... 604/263; 604/162; 604/177; 604/198
(58) Field of Search ................................. 604/263, 198, 604/192, 177, 110, 171, 162, 164.08

(56) References Cited

U.S. PATENT DOCUMENTS 5,549,571 A    8/1996   Sak
5,695,474 A  * 12/1997   Daugherty .................. 604/162
5,951,525 A  *  9/1999   Thorne et al. .............. 604/162

* cited by examiner

*Primary Examiner*—Sharon Kennedy
*Assistant Examiner*—Catherine Serke
(74) *Attorney, Agent, or Firm*—Merchant & Gould P.C.

(57) ABSTRACT

An injection needle device includes an injection needle; a holder holding the base end of the injection needle and having a through hole in communication with the injection needle; a tube through which a liquid medicine can flow; a connector connecting the holder and the tube so that they are in communication with each other; a cylindrical stretchable member capable of stretching or contracting in an axial direction, one end of the member being connected to at least one of the holder, the tube and the connector; and a cylindrical protector through which the injection needle passes, the protector being provided with a wing and being connected to another end of the stretchable member. In this injection needle device, the stretchable member is stretched or contracted so as to slide said protector to change its position with respect to the injection needle within a range including a position in which the tip of the injection needle is completely contained in the protector, whereby an exposed length of the injection needle exposed from the protector can be changed into a desired length. The stretchable member itself can maintain a certain stretched or contracted state.

11 Claims, 6 Drawing Sheets

WINGED INJECTION NEEDLE DEVICE

FIELD OF THE INVENTION

The present invention relates to a winged injection needle device having a cover for containing an injection needle after use.

BACKGROUND OF THE INVENTION

Conventionally, in medical facilities, there have been problems of contamination or infection due to sticking accidents by being stuck unintentionally by an injection needle, a puncture needle, etc. Recently, in particular, since there has been a possibility that such a sticking accident might cause an infection of hepatitis, AIDS, or the like, therefore increasing social attention is being paid to developments of means for reliably preventing such sticking accidents. However, the medical facilities also have to reduce medical expenses, thus delaying the developments of means and methods for preventing the contamination or infection.

Hitherto, there have been proposed various covers and means in order to prevent such sticking accidents from occurring when containing the used injection needles or puncture needles in the cover. Most of such proposed covers aim to safely cover an injection needle without having wings. In the meantime, the present invention is directed to a covering means for a winged injection needle that frequently is used in a procedure such as a liquid infusion, a blood transfusion, extracorporeal blood circulation, or the like.

A winged injection needle device includes an injection needle, a needle base for fixing the injection needle, and a tube connected to the needle base. Most of the means for preventing sticking accidents are formed so that the injection needle and the needle base can move relative to each other in order to prevent sticking accidents after use. Conventional means roughly can be classified into two types: a device having a wing attached to an injection needle or a needle base; and a device having a wing attached to a cover. The injection needle of the present invention belongs to the latter type.

The latter type of injection needle is disclosed in, for example, U.S. Pat. No. 5,549,571 A. In a structure of the injection needle device disclosed in this patent, a wing is attached to a hub in which an injection needle penetrates, and the hub is connected to the needle base via a stretchable connection part. Therefore, by stretching or contracting the connection part, it is possible to cover the injection needle by the hub or expose the needle.

However, in the stretchable connection part constituting the means for preventing sticking accidents in the injection needle device of the above-mentioned U.S. patent, practical working property, manufacturing cost, and the like are not sufficiently and specifically considered. Furthermore, there remain some problems to be improved in terms of the entire configuration of the injection needle device, for example, simpleness of the structure and easiness of manufacture.

SUMMARY OF THE INVENTION

It is an object of the present invention to solve the problems of the prior art mentioned above. That is, the object of the present invention is to provide a winged injection needle device satisfying the following three conditions: (1) it is possible to contain a used injection needle safely and easily; (2) a structure is simple and the manufacturing cost is low, and (3) a used injection needle device can be disposed of sanitarily.

In order to solve the above-mentioned problems, the winged injection needle device of the present invention includes an injection needle; a holder holding the base end of the injection needle and having a through hole in communication with the injection needle; a tube through which a liquid medicine can flow; a connector connecting the holder and the tube so that they are in communication with each other; a cylindrical stretchable member capable of stretching or contracting in an axial direction, one end of the member being connected to at least one of the holder, the tube and the connector; and a cylindrical protector through which the injection needle passes, the protector being provided with a wing and being connected to another end of the stretchable member. In the injection needle device, the stretchable member is stretched or contracted so as to slide the protector to change its position with respect to the injection needle within a range including the position in which the tip of the injection needle is completely contained in the protector, whereby an exposed length of the injection needle exposed from the protector can be changed into a desired length, and the stretchable member itself can maintain a certain stretched or contracted state.

According to the above-mentioned configuration, the exposed length of the injection needle can be changed freely and its state can be maintained. Therefore, users do not have to select injection needles having a different length depending upon injection sites or other factors. Thus, the injection needle device can been used extremely easily.

It is preferable in the above-mentioned configuration that the stretchable member has an accordion structure. With such a configuration, functions required for the stretchable member can be attained easily.

It is further preferable that the stretchable member is made of polyolefine.

It is still further preferable that the stretchable member has an accordion-structured part and has a stretching ratio, which is a ratio of the length of the accordion-structured part stretched to the maximum with respect to the length of the accordion-structured part contracted to the minimum, in the range from 2.5 to 3.6. With such a configuration, the force required for stretch or contraction of the accordion-structured part can be optimized and a length of the needle tube or a hole diameter of the accordion-structured part can be set to a necessary and sufficient size.

It is still further preferable that a difference between the stretched length and the contracted length of the stretchable member is larger than the maximum exposed length of the injection needle. With such a configuration, the injection needle reliably can be contained in the protector.

It is further preferable that the wing is rotatably attached to a cylindrical part of the protector. With such a configuration, the angular relationship between the injection needle and the wing optionally can be adjusted without affecting the stretchable member in use, and the direction of the needle can be selected when sticking the needle.

It is still further preferable that a cavity diameter at the tip of the protector is 1.1 to 2.0 times the diameter of the injection needle. Thus, such a configuration facilitates maintaining of the tip of the injection needle when sticking the needle, and sliding of the injection needle when it is covered and contained.

It is further preferable that the tip of the protector is provided with a means for preventing the re-protrusion of the injection needle contained in a cavity of the protector.

It is further preferable that the connector has a first part and a second part, the tube is fitted onto the outer surface of the second part, the holder is directly or indirectly connected to a cavity of the first part of the connector, and the stretchable member is fitted onto the outer surface of the first part of the connector. With such a configuration, it is possible to reliably fix the stretchable member and easily manufacture the device.

According to another aspect of the present invention, a winged injection needle device includes an injection needle; a holder holding the base end of the injection needle and having a through hole being in communication with the injection needle, an anchoring member provided on the holder; a tube in which a liquid medicine can flow; a connector having an engaging part capable of engaging the anchoring member provided on the holder and connected to the tube, a cylindrical stretchable member capable of stretching or contracting in an axial direction, one end of the member being coupled to at least one of the tube and the connector; and a cylindrical protector provided with a wing through which the injection needle passes and coupled to another end of the stretchable member. In the injection needle device, the stretchable member is stretched or contracted so as to slide the protector to change its position with respect to the injection needle within a range including the position in which the tip of the injection needle is completely contained in the protector, whereby an exposed length of the injection needle exposed from the protector can be changed into a desired length. Furthermore, the holder and the connector are not connected to each other in an initial state, and they are irreversibly connected to each other by contracting the stretchable member so as to engage the anchoring member of the holder with the engaging part of the connector.

It is preferable that the connector is a hollow cylinder and has a catch on the inner surface, the anchoring member includes a pair of elastic legs and each of the tips of the elastic legs is provided with an engaging latch, and the inner diameter of the connector is larger than the external size of the tip of the engaging part and smaller than the external size of the engaging latch.

As mentioned above, according to the winged injection needle of the present invention, it is possible to prevent sticking accidents by being unintentionally stuck by an injection needle after a user finished a procedure on a patient. Consequently, it is possible to avoid the infection or contamination caused by sticking accidents. Furthermore, since the cover containing the injection needle can be disposed of sanitarily, the contamination and/or infection of persons other than the users can be prevented. In addition, the winged injection needle device of the present invention has a simple structure and can be manufactured at low cost, and therefore it can be widely used for medical instruments.

DETAILED DESCRIPTION OF THE INVENTION

Hereinafter, the present invention will be described by way of embodiments with reference to drawings.

(First Embodiment)

Figure 1:
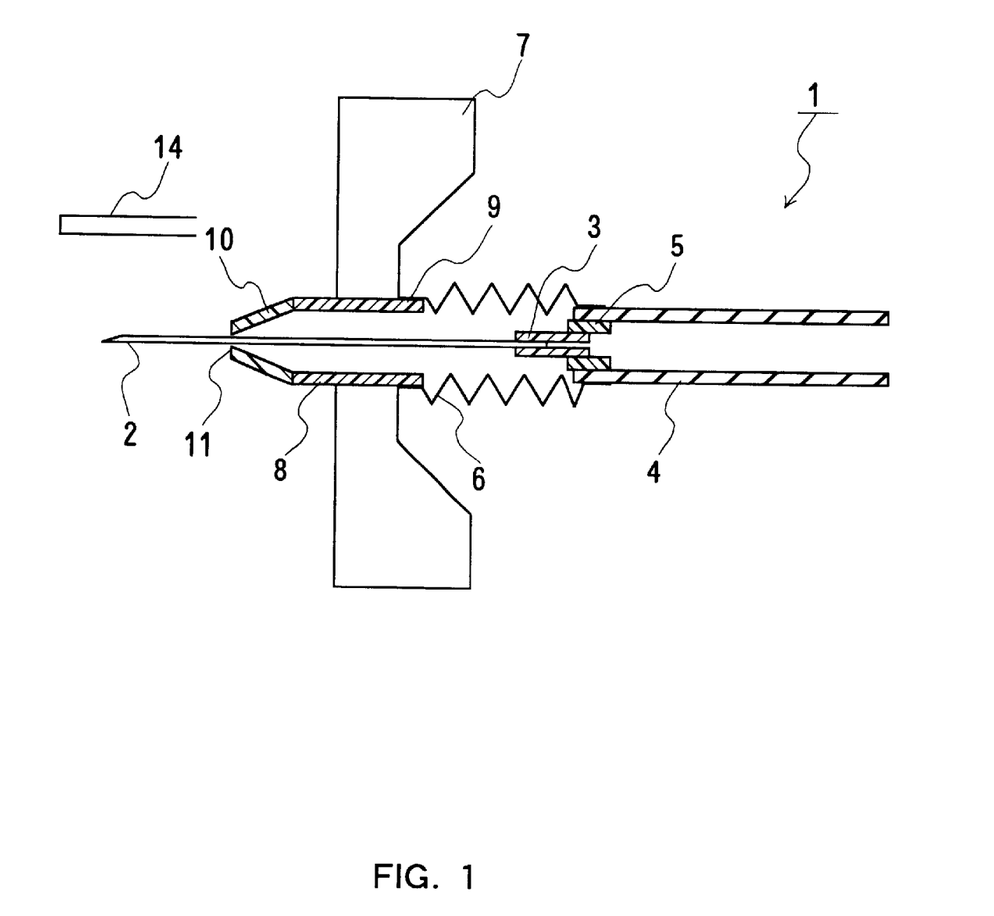
FIG. 1 is a schematic cross-sectional view showing a winged injection needle device according to a first embodiment of the present invention.

The schematic structure of a winged injection needle device according to the first embodiment of the present invention will be described with reference to FIG. 1. The winged injection needle device 1 of the present invention has a liquid medicine passageway including an injection needle 2, a cylindrical holder 3 tightly fixing the injection needle 2, a tube 4 of polyvinyl chloride resin, for example, through which a liquid medicine can flow, and a cylindrical connector 5 connecting the holder 3 and the tube 4. The injection needle device further includes a cylindrical stretchable member 6 made of polyethylene and having an accordion structure, and a protector 8 having a pair of wings 7 at both sides. Members constituting the above-mentioned liquid medicine passageway extend through the cavity of the stretchable member 6 and the protector 8.

The holder 3 is fitted into a through hole of the connector 5, and the tube 4 is fitted onto the outside of the connector 5. One end of the stretchable member 6 is fitted onto the outside of the end of tube 4 that is fitted onto the connector 5. Another end of the stretchable member 6 is fitted onto the protector base end 9 of the protector 8. Herein, the holder 3 and the connector 5 may be formed as one unit. In such a case, one end of the stretchable member 6 may be fitted onto any one of the tube 4, the holder 3, and the connector 5. The stretchable member 6 is tightly fixed to the connection part of the protector base end 9 and to the end of the tube 4 (or the connector 5) so as not to be easily detached when the stretchable member 6 is stretched.

The protector tip 10 of the protector 8 has a pore 11. The injection needle 2 penetrating through the cavity of the protector 8 can be exposed from the pore 11 or retracted into the protector 8. The protector tip 10 is tapered off so that the injection needle does not move when the needle is stuck into the patient's body. The diameter of the pore 11 is of a size larger than that of the injection needle. A needle cap 14 is placed on the tip of the injection needle 2.

The cylindrical stretchable member 6 is made, for example, of polyethylene and is capable of stretching or contracting in an axial direction by its accordion structure. The stretch or contraction of the stretchable member 6 permits the protector 8 to slide on the outside of the injection needle 2. Thereby, the injection needle 2 can be covered with and contained in the protector 8 or can be exposed from the protector 8. Furthermore, the accordion structure is formed so that it can maintain a stretched or contracted state after the external force applied to the accordion structure is removed (free state). Therefore, the stretchable member 6 can maintain the desired length of the stretched state within the stretchable range. As a result, the length of the injection needle 2 exposed from the protector 8 (hereinafter, an "exposed length" will be referred to) optionally can be adjusted within the predetermined range. When the exposed length of the injection needle 2 can be changed optionally, users do not have to select injection needles having a different length depending upon the injection sites or other factors, thus facilitating the procedure with the injection needle device. In particular, this device makes it possible to finely adjust the exposed length, which cannot be attained by using the standard length of the needle. Therefore, this device is useful in clinical treatment in which various cases are required to be treated. In order to provide the stretchable member 6 with a function capable of maintaining the optional stretching state, a well-known toggle structure such as that of a stretchable straw may be used. Therefore, the details are not described herein.

Furthermore, in order to attain a function for avoiding sticking accidents more reliably, it is desirable to cover and contain the injection needle 2 completely after using the injection needle device. Therefore, it is necessary that the protector can contain the injection needle 2 completely when the stretchable member 6 is stretched to the maximum.

Furthermore, in order to design a right length of the needle or the stretchable member 6, it is important to set an exposed length of the needle and a stretch-contract difference (difference between a length of the stretchable member 6 stretched to the maximum and a length of the stretchable member 6 contracted to the minimum). That is, it is desirable that the stretch-contract difference of the stretchable member 6 is larger than the maximum exposed length of the injection needle. The maximum exposed length of the injection needle substantially is determined depending upon the applications of use. Consequently, the practically necessary stretch-contract difference also is determined. In the accordion structure as in this embodiment, the stretch-contract difference is effected by the length of the part of the stretchable member 6 capable of stretching or contracting, and therefore the length of the stretchable member 6 is also determined. That is, it is wasteful if the stretch-contract difference is too much larger than the maximum exposed length of the injection needle, which may lead to an uncertainty when sticking the needle into the patient body. On the contrary, when the stretch-contract difference is too smaller with respect to the exposed length, there may be a fear that the injection needle 2 cannot be covered sufficiently with and contained in the protector 8 after use. Therefore, it is not desirable in terms of the prevention of sticking accidents.

A material for the stretchable member 6 is not particularly limited and any materials can be used as long as they are capable of plastically stretching or contracting and capable of maintaining the stretched state. For example, a material used for a drinking straw, etc. can be used. A preferable example of the material for the stretchable member 6 includes polyolefin such as polyethylene, polypropylene, etc., polyvinyl chloride resin, and the like. A material for the protector is not particularly limited and any materials can be used, for example materials used for a needle base and a wing of a conventional winged injection needle device. Moreover, the protector 8 and the wing 7 may be made of different members, respectively. Occasionally, it is rather desirable that the protector 8 and the wing 7 are made of different members in terms of the application or function. It is because the wing 7 generally requires a flexibility so as to easily follow the skin, while the protector 8 requires the hardness so as to hold and contain the injection needle 2. When the wing 7 and the protector 8 are separately formed and the wing 7 is rotatably attached around the protector 8, a user conveniently can select the direction of the injection needle when sticking the needle into a patient body.

It is preferable that the diameter of the pore 11 of the protector tip 10 is 1.1 to 2.0 times the diameter of the injection needle 2. It is sufficient that the cavity of the protector tip 10 has a diameter such that the injection needle 2 can smoothly penetrate through the cavity. When the diameter is too large, the needle tip cannot be well maintained at the time of sticking. On the contrary, when the diameter is too small, it is difficult for the injection needle to freely slide when the injection needle is covered and contained.

A method for using the winged injection needle device of this embodiment will be briefly explained. As shown in FIG. 1, the needle cap 14 is removed; then the injection needle 2 is stuck into a patient's body while holding the wing 7 so as to administer the liquid solution into the patient body after sticking; thereafter (after the injection procedure), the winged injection needle device 1 is retracted from the patient's body; and the stretchable member 6 is drawn by holding both the base end of the tube 4 or the stretchable member 6 and the protector 8 so that the stretchable member 6 is stretched. As the stretchable member 6 is stretched, the exposed injection needle 2 can be contained in the cavity of the protector 8. In this state, the winged injection needle device 1 as a whole is disposed of. Since the injection needle 2 is covered, the risk of sticking accidents in the disposal process, etc. is reduced.

(Second Embodiment 2)

Figure 2:
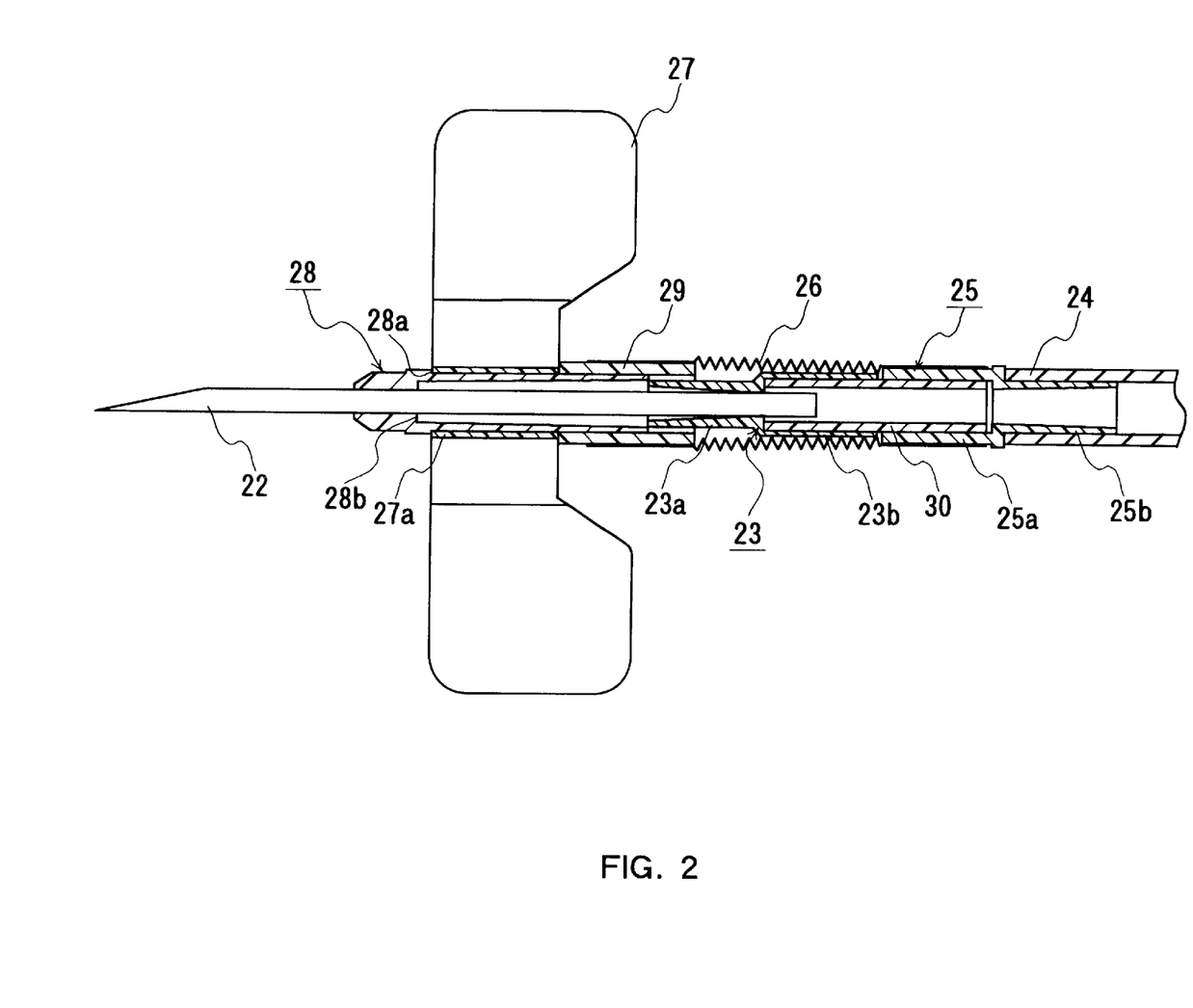
FIG. 2 is a schematic cross-sectional view showing a winged injection needle device according to a second embodiment of the present invention.
Figure 3:
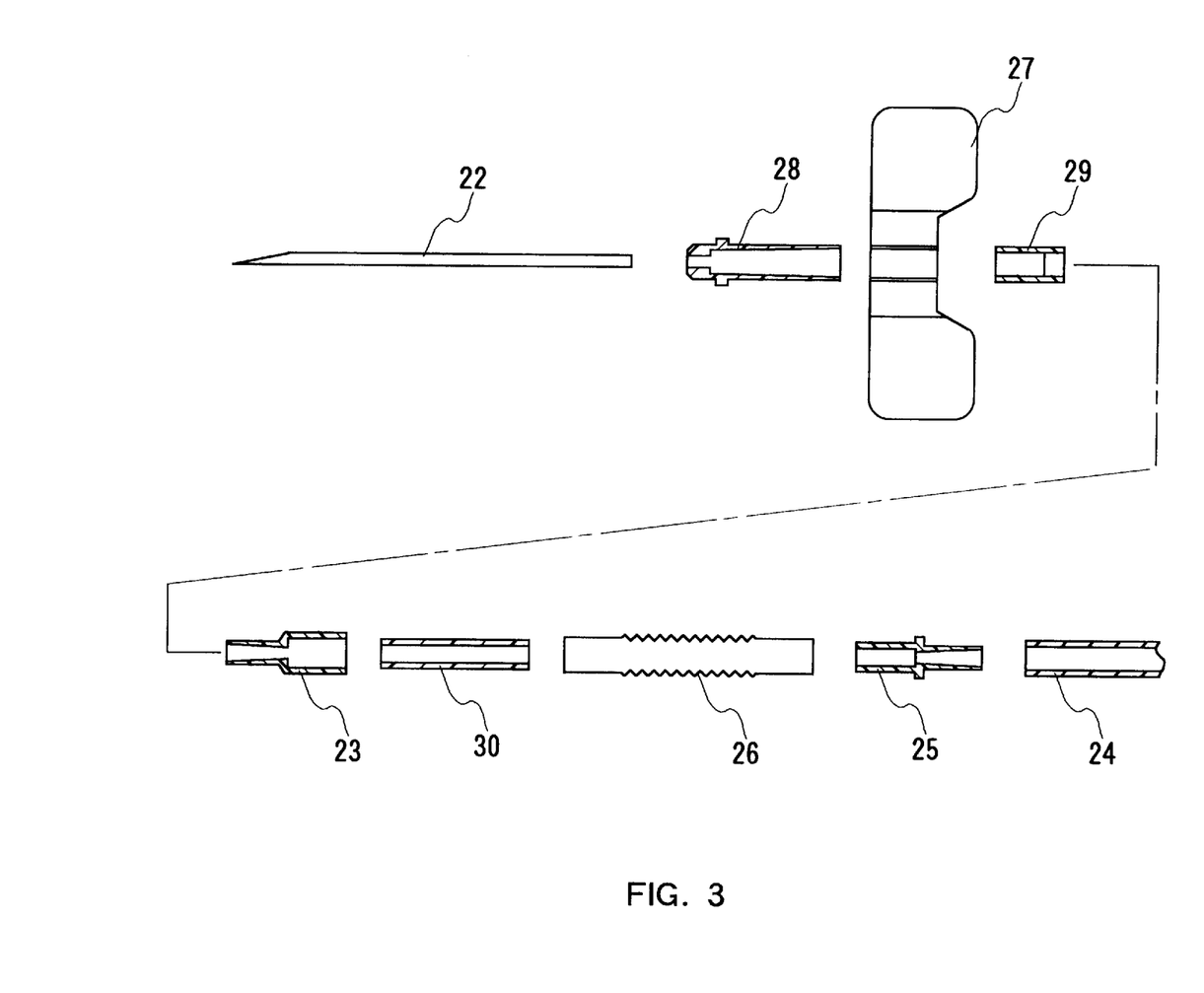
FIG. 3 is an exploded cross-sectional view showing the winged injection needle device of FIG. 2.

FIG. 2 is a schematic cross-sectional view showing a winged injection needle device according to a second embodiment of the present invention. FIG. 3 is an exploded cross-sectional view showing the device of FIG. 2. The injection needle 22 is held in a through hole of a cylindrical holder 23. The holder 23 includes a small-diameter part 23a positioned at the side of the injection needle 22 and a large-diameter part 23b positioned at the rear part of the small-diameter part 23a. The injection needle 22 is fitted into the small-diameter part 23a so as to be held. One end of a connecting pipe 30 is fitted into the large-diameter part 23b. Another end of the connecting pipe 30 is fitted into a first part 25a of a cylindrical connector 25. Therefore, the holder 23 and the connector 25 are connected to each other via the connecting pipe 30. A tube 24 is fitted onto the second part 25b of the connector 25. The first part 25a has a diameter larger that that of the second part. However, it is not necessary that the diameters are in such relation, provided that the injection needle 22 can be held by and the tube 24 is fitted onto the respective part of the connector 25. As mentioned above, the members from the tube 24 to the injection needle 22 form one through hole.

Reference numeral 28 denotes a cylindrical protector and it can slide on the outer surface of the injection needle 22. A wing 27 is attached to the protector 28 at a hub 27a that is positioned at the center of the wing 27 and can rotate around the outer surface of the protector 28. An outer surface step 28a provided at the outer surface of the protector 28 prevents the wing 27 from moving in the direction toward the injection needle 22. Also, a wing stopper 29 provided at the rear part of the protector 28 prevents the wing 27 from moving in the direction toward the base end of the injection needle 22.

Reference numeral 26 denotes a stretchable member. One end of the stretchable member 26 is fitted onto the outside of the wing stopper 29 to be secured, and another end is fitted onto the first part 25a of the connector 25 to be secured. Materials etc. of the stretchable member 26 are as the same as those of the first embodiment shown in FIG. 1.

As in the first embodiment, stretch or contraction of the stretchable member 26 permits the protector 28 to slide on the outside of the injection needle 22. Thereby, the injection needle 22 can be covered with and contained in the protector 28 or can be exposed from the protector 28. Furthermore, the accordion structure is formed so that it can maintain a stretched or contracted state after the external force applied to the accordion structure is removed (free state). Therefore, the stretchable member 26 can maintain the desired length of the stretched state within the stretchable range. As a result, the length of the injection needle 22 exposed from the protector 28 optionally can be adjusted within the predetermined range.

When the accordion structure is employed for the stretchable member 26, a stretching ratio, which is a ratio of a length of the accordion-structured part stretched to the maximum with respect to the length thereof contracted to the minimum, is set to be in the range from 2.5 to 3.6. The range of the stretching ratio is determined as follows.

The stretching ratio of the accordion structure is determined in accordance with a wall thickness of materials and the pitch of accordion folds. The wall thickness of the material used such kind of the accordion structure is generally in the range from 0.18 to 0.25 mm. Too small a wall thickness does not provide a sufficient strength. Too large a wall thickness makes it difficult to increase the stretching ratio. Therefore, the practical range of the wall thickness used for the injection needle device of the present invention should be further limited than the above-mentioned range. Thus in the practical range, the wall thickness is sufficiently small that it does not affect the stretching ratio and the stretching ratio is determined in accordance with only the pitch of the accordion folds. Furthermore, since the force required for stretch or contraction depends on the pitch of accordion folds, in the injection needle device according to the invention, the force is substantially determined in accordance with the stretching ratio. That is, the larger the stretching ratio is, the larger the force required for stretch or contraction is.

The characteristics required for the accordion-structured part used for the injection needle device of the present invention are such that a force required for stretch or contraction is appropriate, and the stretching ratio is sufficiently large, in addition to an appropriate strength.

If the force required for stretch or contraction is small, it is difficult to maintain a certain stretched or contracted state stably, thus making it inconvenient to handle in use. Furthermore, if the stretching ratio is small, it is necessary to increase the length of the accordion-structured part when it is contracted to the minimum, in order to attain the predetermined stretch-contract difference. As a result, the size of the entire injection needle device is increased and at the same time the cost for the material is increased. Therefore the stretching ratio should be 2.5 or more.

On the other hand, too large a stretching ratio is not preferable for the following reasons.

Too large a stretching ratio means too large a force is required for stretch or contraction. Such a too large required force causes difficulty in stretching or contracting the accordion-structured part when the injection needle is in the patient's body. Furthermore, if the stretching ratio, i.e., the pitch is increased, the difference between the inner diameter and the outer diameter of the accordion-structured part in its contracted condition is increased. Since it is difficult to reduce the inner diameter because of the size of the contained member, the outer diameter has to be increased to obtain the increased stretching ratio. Thus the increased stretching ratio makes the size of the injection needle device large. Therefore, the practical upper limit of the stretching ratio should be 3.6.

As mentioned above, it is found that the appropriate stretching ratio is set to be in the range from 2.5 to 3.6 from the viewpoint of the conditions required for the injection needle device and the practical selecting range of the wall thickness and the pitch.

The inner diameter of the protector 28 is small at the tip and slightly larger at the rear part. The protector 28 is provided with an inner surface step 28b. The diameter of the small-diameter part is the same as that of the pore 11 of the protector tip 10 in the first embodiment.

Figure 4:
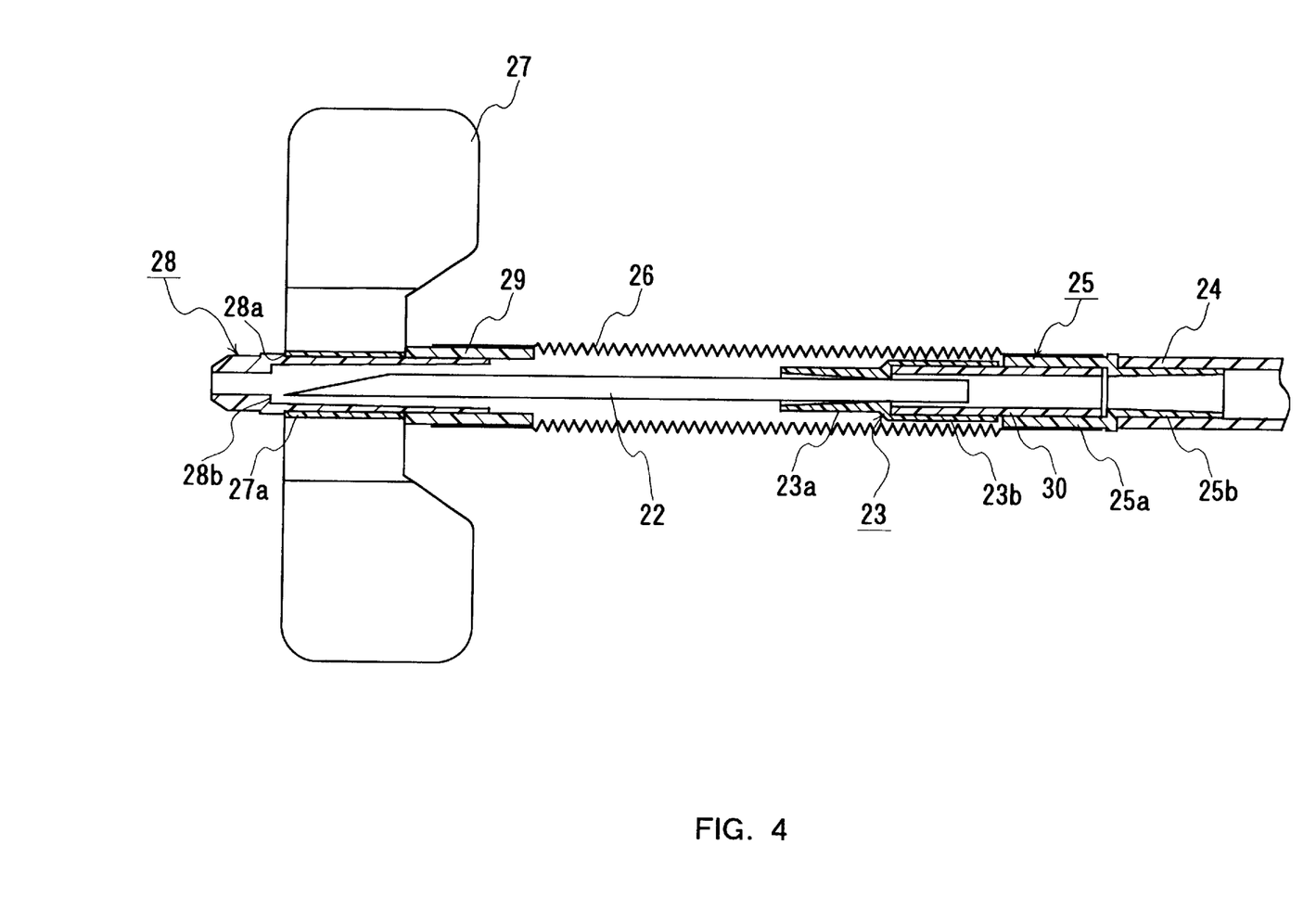
FIG. 4 is a schematic cross-sectional view showing an operation of the injection needle device of FIG. 2.

FIG. 4 shows a state in which the injection needle 22 is contained in the protector 28 by stretching the stretchable member 26 in the injection needle device having the above-mentioned configuration. In this state, the injection needle 22 does not easily protrude from the protector 28. That is, the tip of the injection needle 22 is brought into contact with the inner surface step 28b of the protector 28, thereby being prevented from protruding. In order to protrude the injection needle 22, it is necessary to adjust the tip of the injection needle 22 to the tip hole of the protector 28. Therefore, the possibility of accidental protrusion is reduced.

According to this embodiment, it is made to be extremely easy to manufacture the winged injection needle device, because of the rational structure of connecting each member. More specifically, the feature of the structure is that the tube 24 is fitted onto the small-diameter part 25b of the connector 25; the holder 23 is connected to the large diameter part 25a of the connector 25 via the connecting pipe 30; and the stretchable member 26 is fitted onto the outer surface of the large-diameter part 25a of the connector 25. Thereby, the stretchable member 26 can be connected reliably to the base end of the injection needle 22. Furthermore, it is possible to connect the members from the injection needle 22 to the tube 24, and to couple the stretchable member 26 to the above-mentioned connected members by a simple structure.

(Third Embodiment)

Figure 5:
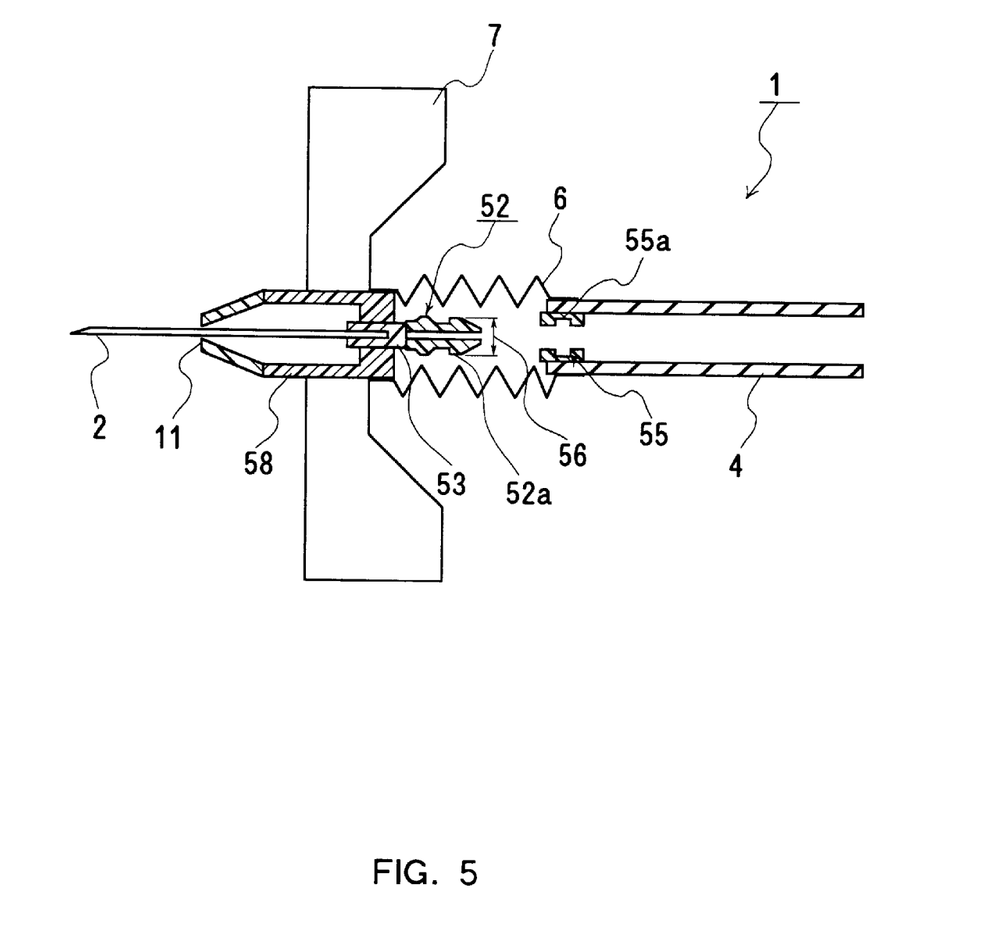
FIG. 5 is a schematic cross-sectional view showing a winged injection needle device according to a third embodiment of the present invention.

The winged injection needle device of the third embodiment according to the present invention will be described with reference to FIG. 5. The same elements as those of FIG. 1 are given to the same numbers and the explanations are not repeated herein. In this embodiment, the holder 53 to which the injection needle 2 is fixed is detachably held in the cavity of the protector 58. An anchoring member 52 including a pair of elastic legs is attached to the rear end of the holder 53. Anchoring latches 52a are respectively formed on the elastic legs of the anchoring member 52. Anchoring catches 55a are formed on the inner surface of the cylindrical connector 55 attached to the tube 4. The external size 56 of the anchoring latches 52a of the anchoring member 52 is larger than the inner diameter of the connector 55. Therefore, by fitting the anchoring latches 52a into the connector 55a, the anchoring member 52 is anchored to the connector 55. Consequently, the injection needle 2 is coupled to the connector 55. Furthermore, since the external size of the tip of the elastic legs of the anchoring member 52 is smaller than the inner diameter of the connector 55, the anchoring member 52 easily can be inserted into the connector 55.

As mentioned above, the connector 55 is not connected to the holder 53 in the initial state. The connector 55 is connected to the holder 53 by moving the anchoring member 52 with holding the protector 58 so as to anchor to the connector 55.

Moreover, the force of holding the anchoring member 52 to the connector 55 is larger than the force of holding the holder 53 in the cavity of the protector 58. Therefore, when the holder 53 is connected to the connector 55, by stretching the stretchable member 6 while holding the protector 58, the holder 53 is detached from the cavity of the protector 58 while the connection between the holder 53 and the connector 55 is maintained.

A method for using the winged injection needle device of this embodiment will be briefly explained. Prior to the procedure, the holder 53 is detachably fitted into the cavity of the protector 58. After the same procedure as in the previous embodiment, the stretchable member 6 is contracted thus to bring the holder 53 closer to the connector 55 so as to fit the anchoring member 52 into the cavity of the connector 55. When the tube 4 is drawn in the direction in which the tube is taken apart from the protector 58, the holder 53 that was non-securably fitted into the protector 58 is detached from the protector 58 while the holder 53 is connected to the connector 55 as the stretchable member 6 is stretched. As a result, the injection needle 2 is covered with and contained in the protector 58.

(Fourth Embodiment)

Figure 6:
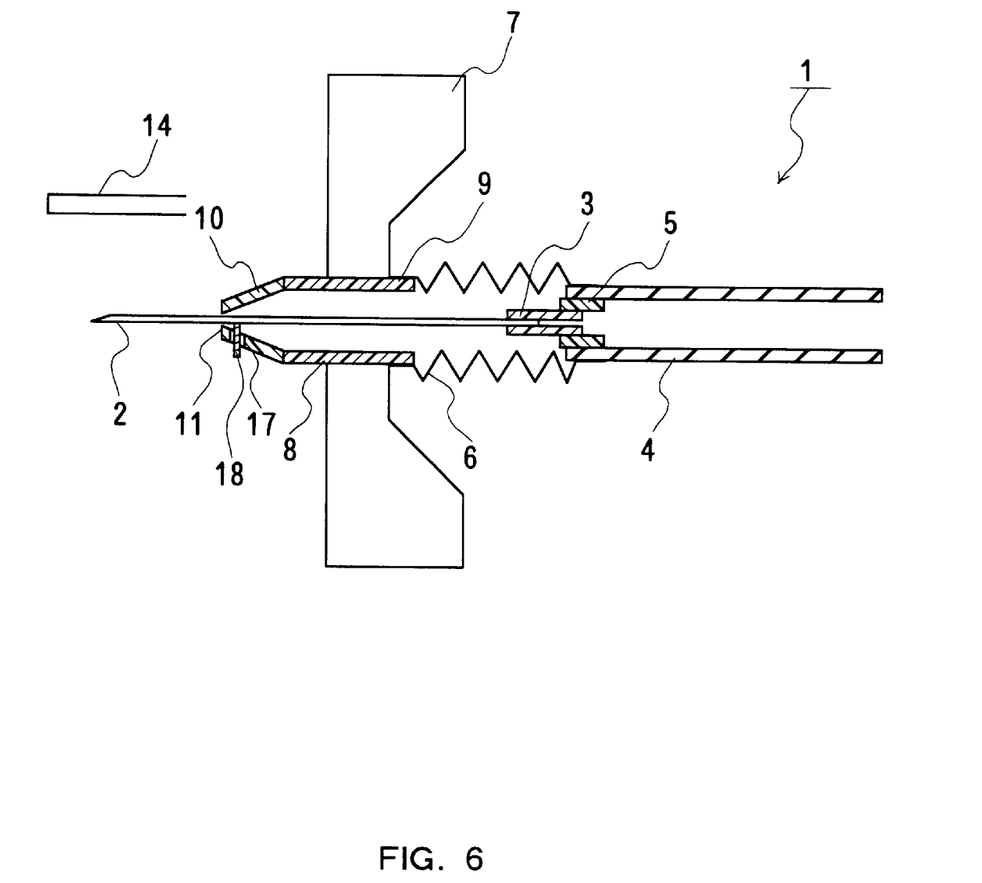
FIG. 6 is a schematic cross-sectional view showing a winged injection needle device according to a fourth embodiment of the present invention.

FIG. 6 is a schematic cross-sectional view showing a winged injection needle device according to a fourth embodiment of the present invention. The same elements as those of FIG. 1 are given to the same numbers and the explanations are not repeated herein.

In this embodiment, a slit 17 is formed on the tip of the protector 8. Reference numeral 18 denotes a protrusion prevention stopper, which is movably attached so that it can pass through the slit 17 and be inserted into the cavity of the protector 8. The protrusion prevention stopper 18 is inserted into the cavity of the protector 8, thereby preventing the injection needle 2 from protruding.

Herein, the slit 17 may be replaced by a hole. In addition, the stopper 18 may be provided in a package together with the injection needle, to be attached to the device if necessary, instead of attaching the stopper 18 to the protector from the beginning.

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description, all changes that come within the meaning and range of equivalency of the claims are intended to be embraced therein.

What is claimed is:

1. A winged injection needle device comprising:
   an injection needle;
   a holder holding a base end of said injection needle and having a through hole being in communication with said injection needle;
   a tube through which a liquid medicine can flow;
   a connector connecting said holder and said tube so that they are in communication with each other;
   a cylindrical stretchable member capable of stretching or contracting in an axial direction, one end of the member being connected to at least one of said holder, said tube and said connector; and
   a cylindrical protector through which said injection needle passes, the protector being provided with a wing and being connected to another end of said stretchable member,
   wherein said stretchable member is stretched or contracted so as to slide said protector to change its position with respect to said injection needle within a range including a position in which a tip of said injection needle is completely contained in said protector, whereby an exposed length of said injection needle exposed from said protector can be changed into a desired length, and
   said stretchable member itself can maintain a certain stretched or contracted state.

2. The winged injection needle device according to claim 1, wherein said stretchable member has an accordion structure.

3. The winged injection needle device according to claim 2, wherein said stretchable member is made of polyolefin.

4. The winged injection needle device according to claim 1, wherein said stretchable member has an accordion-structured part and has a stretching ratio, which is a ratio of the length of said accordion-structured part stretched to the maximum with respect to the length of the accordion-structured part contracted to the minimum, in the range from 2.5 to 3.6.

5. The winged injection needle device according to claim 1, wherein a difference between the stretched length and contracted length of said stretchable member is larger than a maximum exposed length of said injection needle.

6. The winged injection needle device according to claim 1, wherein said wing is rotatably attached to a cylindrical part of said protector.

7. The winged injection needle device according to claim 1, wherein a cavity diameter at a tip of said protector is 1.1 to 2.0 times the diameter of said injection needle.

8. The winged injection needle device according to claim 1, wherein a tip of said protector is provided with a means for preventing the re-protrusion of the injection needle contained in the cavity of said protector.

9. The winged injection needle device according to claim 1, wherein said connector has a first part and a second part, said tube is fitted onto the outer surface of said second part, said holder is directly or indirectly connected to a cavity of the first part of said connector, and said stretchable member is fitted onto the outer surface of the first part of said connector.

10. A winged injection needle device comprising
    an injection needle,
    a holder holding the base end of said injection needle and having a through hole being in communication with said injection needle,
    an anchoring member provided on said holder,
    a tube though which a liquid medicine can flow,
    a connector having an engaging part capable of engaging the anchoring member provided on said holder and connected to said tube,
    a cylindrical stretchable member capable of stretching or contracting in an axial direction, one end of the member being coupled to at least one of said tube, and said connector, and
    a cylindrical protector provided with a wing through which said injection needle passes and coupled to another end of the stretchable member,
    wherein said stretchable member is stretched or contracted so as to slide said protector to change its position with respect to said injection needle within a range including a position in which a tip of said injection needle is completely contained in said protector, whereby an exposed length of said injection needle exposed from said protector can be changed into a desired length, and
    wherein said holder and said connector are not connected to each other in an initial state, and they are irreversibly connected to each other by contracting said stretchable member so as to engage the anchoring member of said holder with the engaging part of said connector.

11. The winged injection needle device according to claim 10, wherein said connector is a hollow cylinder and has a catch on the inner surface; said anchoring member includes a pair of elastic legs and each of the elastic legs is provided with an engaging latch; and the inner diameter of said connector is larger than the external size of a tip of said engaging part and smaller than the external size of said engaging latch.

* * * * *